US00PP33848P2

(12) United States Plant Patent
Arts

(10) Patent No.: US PP33,848 P2
(45) Date of Patent: Jan. 11, 2022

(54) ***HYDRANGEA* PLANT NAMED 'H220912'**

(50) Latin Name: *Hydrangea macrophylla*
Varietal Denomination: H220912

(71) Applicant: HYDRANGEA BREEDERS ASSOCIATION B.V., De Kwakel (NL)

(72) Inventor: Niels Arts, Aalsmeer (NL)

(73) Assignee: HYDRANGEA BREEDERS ASSOCIATION B.V., De Kwakel (NL)

( * ) Notice: Subject to any disclaimer, the term of this patent is extended or adjusted under 35 U.S.C. 154(b) by 0 days.

(21) Appl. No.: 17/240,915

(22) Filed: Apr. 26, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

(56) References Cited

PUBLICATIONS https://www.floraldaily.com/article/9313213/nl-new-pot-hydrangeas-test-well-for-shelf-life/; Apr. 20, 2021; 2 pages.*
https://www.hydrangeabreeders.nl/wp-content/uploads/2021/01/Catalogus-2021-2022-HBA-Potplanten-Paniculata-28MB.pdf; Aug. 11, 2021; 3 pages.*

* cited by examiner

*Primary Examiner* — Kent L Bell
(74) *Attorney, Agent, or Firm* — C. Anne Whealy

(57) ABSTRACT

A new and distinct cultivar of *Hydrangea* plant named 'H220912', characterized by its relatively compact, upright and uniformly mounded plant habit; vigorous growth habit and rapid growth rate; freely branching habit with strong, thick and sturdy stems; freely and uniformly flowering habit; large mophead-type inflorescences with numerous double sterile flowers that are white in color; and good postproduction longevity.

2 Drawing Sheets

Figure 1:
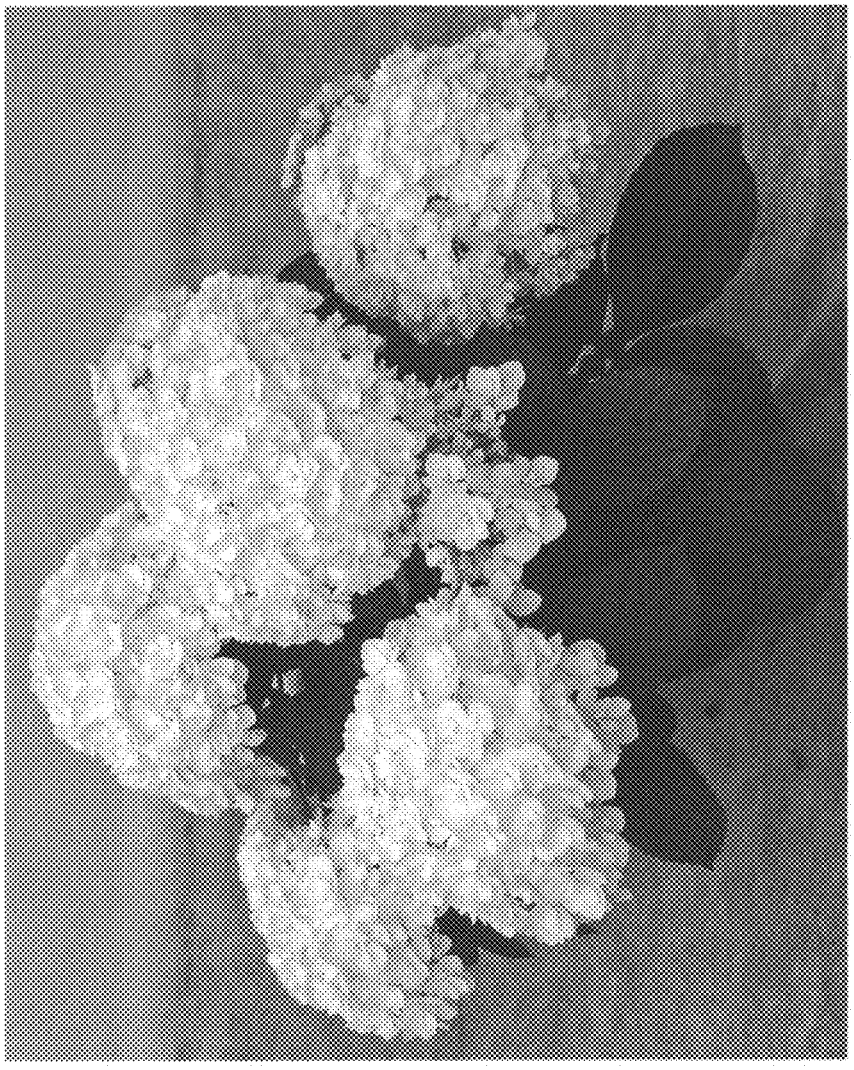

Botanical designation: *Hydrangea macrophylla.*
Cultivar denomination: 'H220912'.

STATEMENT REGARDING PRIOR DISCLOSURES BY INVENTOR & APPLICANT/ASSIGNEE

An European Community Plant Breeder's Rights application for the instant plant was filed by the Applicant/Assignee, *Hydrangea* Breeders Association B.V. of De Kwakel, The Netherlands on Jan. 4, 2021, application number 2021/0008. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H220912'.

The new *Hydrangea* plant is a product of a planned breeding program conducted by the Inventor in De Kwakel, The Netherlands and Glandorf, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor in the spring of 2015 in De Kwakel, The Netherlands, of a proprietary selection of *Hydrangea macrophylla* identified as code number 213108-050, not patented, as the female, or seed, parent with a proprietary selection of *Hydrangea macrophylla* identified as code number 213302-025, not patented, as the male, or pollen, parent. The new *Hydrangea* plant was discovered and selected by the Inventor as a single flowering plant from within the progeny of the stated cross-pollination in a controlled greenhouse environment in Glandorf, Germany in February, 2017.

Asexual reproduction of the new *Hydrangea* plant by vegetative tip cuttings in a controlled environment in Glandorf, Germany since the spring of 2018 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H220912'. These characteristics in combination distinguish 'H220912' as a new and distinct *Hydrangea* plant:

1. Relatively compact, upright and uniformly mounded plant habit.
2. Vigorous growth habit and rapid growth rate.
3. Freely branching habit with strong, thick and sturdy stems.
4. Freely and uniformly flowering habit.
5. Large mophead-type inflorescences with numerous double sterile flowers that are white in color.
6. Good postproduction longevity.

Plants of the new *Hydrangea* can be compared to plants of the female and male parent selections. Plants of the new *Hydrangea* differ primarily from plants of the parent selections in sterile flower type as plants of the new *Hydrangea* have double sterile flowers whereas plants of the parents selection have single sterile flowers.

Plants of the new *Hydrangea* can be compared to plants of the *Hydrangea macrophylla* 'H218915', disclosed in U.S. Plant Pat. No. 32,400. In side-by-side comparisons, plants of the new *Hydrangea* differ primarily from plants of 'H218915' in the following characteristics:

1. Plants of the new *Hydrangea* have slightly larger leaves than plants of 'H218915'.
2. Plants of the new *Hydrangea* have mophead-type inflorescences whereas plants of 'H218915' have lacecap-type inflorescences.
3. Sterile flowers of plants of the new *Hydrangea* are smaller than sterile flowers of plants of 'H218915'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'H220912'.

Figure 2:
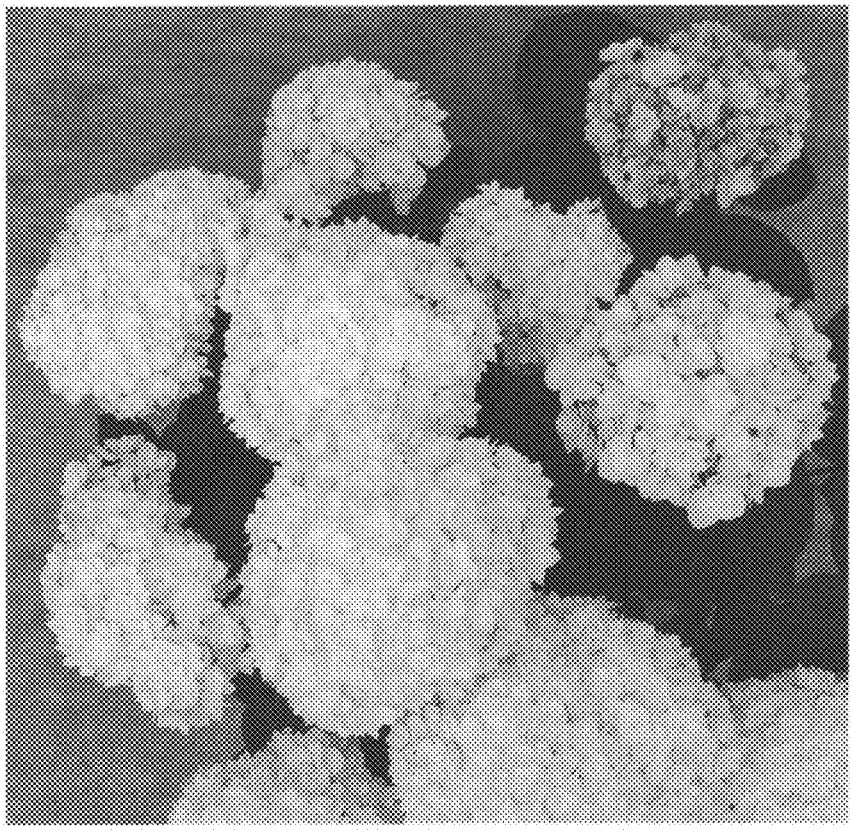

The photograph on the second sheet (FIG. 2) is a close-up view of typical inflorescences of 'H220912'.

DETAILED BOTANICAL DESCRIPTION

Plants used in the aforementioned photographs and in the following description were grown during the late spring and early summer in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were one year old when the photographs and description were taken. Plants of the new *Hydrangea* treated with aluminum sulfate to "blue" the inflorescences do not show any significant color changes. In the following description, color references are made to The Royal Horticultural Society Colour Chart, 2015 Edition, except where general terms of ordinary dictionary significance are used.

Botanical description: *Hydrangea macrophylla* 'H220912'.

Parentage:

- *Female, or seed, parent.*—Proprietary selection of *Hydrangea macrophylla* identified as code number 213108-050, not patented.
- *Male, or pollen, parent.*—Proprietary selection of *Hydrangea macrophylla* identified as code number 213302-025, not patented.

Propagation:

- *Type cutting.*—By vegetative tip cuttings.
- *Time to initiate roots, summer.*—About two weeks at temperatures about 23° C.
- *Time to initiate roots, winter.*—About 18 days at temperatures about 20° C.
- *Time to produce a rooted young plant, summer.*—About four weeks at temperatures about 23° C.
- *Time to produce a rooted young plant, winter.*—About five weeks at temperatures about 20° C.
- *Root description.*—Thick; typically whitish brown in color, actual color of the roots is dependent on substrate composition, water quality, fertilizer type and formulation, substrate temperature and physiological age of roots.
- *Rooting habit.*—Freely branching; dense.

Plant description:

- *Plant and growth habit.*—Upright and uniformly mounded plant habit; strong and sturdy stems; rapid growth rate and vigorous growth habit.
- *Plant height.*—About 25 cm to 35 cm.
- *Plant diameter or area of spread.*—About 45 cm to 50 cm.

Lateral branch description:

- *Branching habit.*—Freely branching habit; when pinched, about nine lateral branches develop per plant.
- *Length.*—About 20 cm.
- *Diameter.*—About 5 mm to 7 mm.
- *Internode length.*—About 2 cm to 5 cm.
- *Texture.*—Smooth, glabrous; fully developed, woody.
- *Aspect.*—Upright to slightly outwardly.
- *Strength.*—Strong, sturdy.
- *Color.*—When developing: Close to 144B; at internodes, close to 185C; lenticels, close to 145C. Developed: Close to 144B; at the internodes, close to 185C; when woody, close to 177C; lenticels, close to 145C.

Leaf description:

- *Arrangement.*—Opposite, simple.
- *Length.*—About 11 cm.
- *Width.*—About 6 cm to 8 cm.
- *Shape.*—Ovate.
- *Apex.*—Cuspidate.
- *Base.*—Obtuse.
- *Margin.*—Dentate to serrate.
- *Texture, upper surface.*—Smooth, glabrous.
- *Texture, lower surface.*—Rugose, glabrous.
- *Venation pattern.*—Pinnate.
- *Color.*—Developing and fully expanded leaves, upper surface: Close to 137A; venation, close to 146D. Developing and fully expanded leaves, lower surface: Close to 137D; venation, close to 146D.
- *Petioles.*—Length: About 1.5 cm to 2 cm. Diameter: About 3 mm. Texture, upper and lower surfaces: Smooth, glabrous. Color, upper and lower surfaces: Close to 146D.

Flower description:

*Flower type and habit*.—Double showy sterile flowers arranged on mophead-type terminal panicles; to date, fertile flower development has not been observed on plants of the new *Hydrangea*; panicles flattened globular in shape; star-shaped flowers face upright to outwardly depending on their position in the inflorescence.

*Fragrance*.—None detected.

*Natural flowering season*.—Plants flower naturally in the early summer and is continuous throughout the summer in Northern Europe.

*Flower longevity*.—Sterile flowers last about four months on the plant, sterile flowers persistent.

*Quantity of flowers*.—Freely flowering habit; about 280 sterile flowers per panicle.

*Panicle height*.—About 6 cm to 8 cm.

*Panicle diameter*.—About 20 cm to 23 cm.

*Sterile flower buds*.—Length: About 3 mm. Diameter: About 3 mm. Shape: Rounded. Color: Close to 145B.

*Sterile flower diameter*.—About 1 cm to 1.5 cm.

*Sterile flower depth* (*height*).—About 5 mm.

*Petals, sterile flowers*.—To date, petal development has not been observed on sterile flowers of plants of the new *Hydrangea*.

*Sepals, sterile flowers*.—Quantity and arrangement: About 14 in about three whorls. Length, outer whorl: About 1.5 cm. Length, inner whorls: About 0.5 cm to 1 cm. Width, outer whorl: About 1 cm to 1.5 cm. Width, inner whorls: About 0.5 cm to 1 cm. Shape: Ovate. Apex: Obtuse. Base: Obtuse. Margin: Entire. Texture, upper and lower surfaces: Smooth, glabrous. Color: When opening, upper and lower surfaces: Close to 145D and 145B. Fully opened, upper surface: Close to NN155D; with development, color becoming closer to 145B; when "blued", inner whorls becoming closer to 155B. Fully opened, lower surface: Close to NN155D; with development, color becoming closer to 145C.

*Pedicels, sterile flowers*.—Length: About 1.5 cm to 2 cm. Diameter: About 2 mm. Strength: Strong. Aspect: Erect to about 45° from vertical. Texture: Smooth, glabrous. Color: Close to NN155D.

*Reproductive organs, sterile flowers*.—Stamens: To date, stamen development has not been observed on plants of the new *Hydrangea*. Pistils: Pistil quantity per flower: About three or four. Pistil length: About 1 mm. Stigma shape: Conical. Stigma color: Close to 155A. Style length: About 1 mm. Style color: Close to 155A. Ovary color: Close to 155A.

*Seeds*.—To date, seed development has not been observed on plants of the new *Hydrangea*.

Pathogen & pest resistance: Under commercial production conditions, plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 3° C. to about 38° C.

It is claimed:

1. A new and distinct *Hydrangea* plant named 'H220912' as illustrated and described.

* * * * *